US012631708B2

(12) United States Patent
Poeck et al.

(10) Patent No.: US 12,631,708 B2
(45) Date of Patent: May 19, 2026

(54) METHOD FOR OPERATING AN IMAGING EXAMINATION DEVICE WHILE TAKING INTO CONSIDERATION A DISTORTED GRADIENT FIELD

(71) Applicant: Otto-von-Guericke-Universität Magdeburg, Magdeburg (DE)

(72) Inventors: Janis Poeck, Magdeburg (DE); Oliver Speck, Magdeburg (DE); Enrico Pannicke, Magdeburg (DE)

(73) Assignee: Otto-von-Guericke-Universität Magdeburg, Madgeburg (DE)

( * ) Notice: Subject to any disclaimer, the term of this patent is extended or adjusted under 35 U.S.C. 154(b) by 391 days.

(21) Appl. No.: 17/773,174

(22) PCT Filed: Oct. 2, 2020

(86) PCT No.: PCT/EP2020/077687
§ 371 (c)(1),
(2) Date: Apr. 29, 2022

(87) PCT Pub. No.: WO2021/083610
PCT Pub. Date: May 6, 2021

(65) Prior Publication Data
US 2024/0151797 A1 May 9, 2024

(30) Foreign Application Priority Data
Oct. 31, 2019 (DE) ..................... 10 2019 129 541.6

(51) Int. Cl.
*G01R 33/565* (2006.01)
*A61B 5/055* (2006.01)
(52) U.S. Cl.
CPC ........ *G01R 33/56572* (2013.01); *A61B 5/055* (2013.01)

(58) Field of Classification Search
CPC .. G01R 33/56572; G01R 33/543; A61B 5/055
See application file for complete search history.

(56) References Cited

U.S. PATENT DOCUMENTS

| | | | |
|---|---|---|---|
| 2006/0012365 A1* | 1/2006 | Werthner ......... | G01R 33/56563 |
| | | | 324/307 |
| 2016/0313434 A1* | 10/2016 | Panther ............ | G01R 33/56572 |
| 2021/0055365 A1* | 2/2021 | Hoshiyama ...... | G01R 33/56572 |

FOREIGN PATENT DOCUMENTS

| | | |
|---|---|---|
| DE | 102005030795 A1 | 7/2006 |
| EP | 1063535 A2 | 12/2000 |
| JP | 2010119740 A | 6/2010 |

OTHER PUBLICATIONS

Julian Maclaren et al, "Prospective motion correction in brain imaging: A review", Magnetic Resonance in Medicine, vol. 69, No. 3, May 8, 2012 (May 8, 2012), pp. 621-636.
(Continued)

*Primary Examiner* — Rishi R Patel
(74) *Attorney, Agent, or Firm* — WCF IP

(57) ABSTRACT

The invention relates to a method for operating an imaging examination device (1), wherein signals are received from an object (5) to be examined and are identified and displayed in layers in the form of sectional images and/or three-dimensional images of the object (5), having the following steps: •a) ascertaining a desired imaging layer (4) of the object (5) to be examined, •b) determining the coordinates of a desired target point (6) in the desired imaging layer (4), •c) determining the coordinates of a corrected target point (6') while taking into consideration a distorted gradient field of the examination device (1) such that the examination device detects an imaging layer on which the desired target point (6) lies on the basis of the distorted gradient field while using the corrected target point (6') instead of the desired target point (6), and •d) detecting an imaging layer (4) by means
(Continued)

a b c of the examination device (1) using the corrected target point
(6') and visualizing an image obtained therefrom.

9 Claims, 2 Drawing Sheets

(56) References Cited

OTHER PUBLICATIONS

David Rotenberg et al, "Real-Time Correction by Optical Tracking
with Integrated Geometric Distortion Correction for Reducing Motion
Artifacts in Functional MRI", Magnetic Resonance in Medicine,
vol. 69, May 14, 2012, pp. 734-748.
Ryan G. Price et al, "Technical Note: Characterization and Correc-
tion of Gradient Nonlinearity Induced Distortion on a 1.0 T Open
Bore MR-SIM", Medical Physics, vol. 42, No. 10, Sep. 22, 2015,
pp. 5955-5960.

* cited by examiner

METHOD FOR OPERATING AN IMAGING EXAMINATION DEVICE WHILE TAKING INTO CONSIDERATION A DISTORTED GRADIENT FIELD

The invention relates to a method for operating an imaging examination device, wherein signals from an object to be examined are recorded and are determined and represented in the form of sectional images of the object. Moreover, the invention relates to a computer program for carrying out such a method and to an examination device for examining an object layer-by-layer. By way of example, the object can be a living being, for example a human or animal.

In general, the invention relates to the field of examining objects layer-by-layer by way of imaging, for example by computed tomography (CT), magnetic resonance imaging (MRI), positron emission tomography (PET), single photon emission computed tomography (SPECT), optical coherence tomography (OCT) and electrical impedance tomography (EIT). Each of these methods may be accompanied by geometric distortions when the images are recorded since the image reconstruction as a rule assumes an error-free geometric image representation, for example a linear image encoder gradient in the case of MRI. In several of the aforementioned examination methods, signals for example are fed into the object to be examined, and corresponding reaction signals, for example altered nuclear spin properties, are recorded. Without loss of generality, the underlying problem will be explained below using the example of magnetic resonance imaging.

In magnetic resonance imaging (MRI), the spatial resolution of the images is attained with the aid of approximately linear magnetic field gradients. The image reconstruction likewise assumes idealized linear image encoding gradients. However, on account of the restricted extent of the field-generating coils, this linearity is only achieved in a small region around the magnetic center. The further the imaging region is away from the center, the greater the geometric distortions in the image representation since the gradient fields deviate from an idealized linear profile. To correct these distortions, the deviations are measured and a correction algorithm is used, the latter displacing the picture elements in accordance with the deviations following the reconstruction. Optionally, this method may also be used to supplement the method according to the invention. This requires an interpolation of the measured data.

The focus here predominantly lies in correcting the incorrect encoding within the measuring layer, that is to say improving the geometric image representation fidelity of the images. In the case of 2-dimensional recordings, a distortion of the plane of the layer itself can only be corrected if appropriate adjacent layers were recorded. To this end, it is advantageous if these adjacent layers were recorded without a gap, that is to say at a distance of zero. A restriction consists in the fact that the layer thickness, as a rule, is greater than the resolution in the layer. Thus, in the case of 2-dimensional imaging, a 2-dimensional correction calculation is only carried out within the plane of the layer, and the deviations out of the plane are neglected. As a consequence, the recorded images may not be localized at the set layer position or may be tilted, and may not show the desired region. Moreover, these images may deviate from the desired planar form, that is to say they may be "bent". This is a problem, for example within the scope of interventional MRI, where fast 2-D sequences with individual layers are used to bring, e.g., an ablation needle to a tumor under image guidance. If these image layers are situated incorrectly, the ablation needle or risk structures are no longer represented as desired. Therefore, interventions are usually carried out in the vicinity of the center of the MRI FOV, where geometric distortions are small. However, as a result, the distance between the physician (outside of the MRI device) and the target structure (near the center) may be very large.

The invention is based on the object of solving the aforementioned problem.

In the case of the method of the type set forth at the outset, the object is achieved by the following steps:

a) defining a desired imaging layer of the object to be examined, b) determining the coordinates of a desired target point in the desired imaging layer, c) determining the coordinates of a corrected target point taking account of a distorted gradient field of the examination device, in such a way that, should the corrected target point be used instead of the desired target point, the examination device, on account of the distorted gradient field, acquires an imaging layer containing the desired target point, and d) acquiring an imaging layer by means of the examination device using the corrected target point, and visualizing an image obtained therefrom.

As a result, simple means can ensure that the imaging layer actually acquired by means of the examination device (feature d) really is the "correct" imaging layer, specifically the desired imaging layer set in each case. Consequently, the invention allows the layer selection to be corrected prospectively during the imaging examination. In contrast to known methods, which are restricted to merely a correction by calculation of already recorded images, the method according to the invention consequently already causes the implementation of a correction before the acquisition of the imaging layer by means of the examination device, in order to ensure that the correct imaging layer is then actually acquired by means of the examination device. In particular, this is very important if interventions are intended to be carried out on the object, e.g., a patient, on the basis of the visualized images in the imaging layer. In particular, the invention allows these interventions to be carried out safely even in regions at a relatively large distance from the magnetic center because the incorrect imaging layer is no longer visualized.

The desired imaging layer of the object to be examined can be defined by way of, e.g., a manual adjustment on the examination device, or by an automatic prescription, for example on the basis of the position of a medical intervention tool in the case of intervention-type procedures. The coordinates of the desired target point may be defined, e.g., by a manual adjustment on the examination device, or by an automatic determination of a point, for example the center, of the desired imaging layer. The same applies to the desired reference point in the desired imaging layer, which reference point will still be mentioned below.

The coordinates of the desired target point and/or of the desired reference point may also be determined by means of a measuring device which is present in addition to the examination device. By way of example, the measuring device can be an external measuring device which acquires the target point, for example by tracking, and determines the coordinates thereof. By way of example, the measuring device can be an optical measuring device. The measuring device may also be part of the examination device, with the measuring device in this case having to carry out a measurement on the basis of a different physical examination principle or at least on the basis of a different sensor to what is used for determining the imaging layer so that it is possible to ensure that the measuring device does not have the same distortions in the signal acquisition as the examination device.

The method according to the invention can be carried out by means of a computer, for example if the method is programmed as a software function. This facilitates a simpler computational correction of the coordinates data. The gradient data of the distorted gradient field may be stored, for example, as a data record in the examination device or in its evaluation apparatus.

According to an advantageous embodiment of the invention, the following features are provided:

a) determining the coordinates of a desired reference point within or outside of the desired imaging layer, said reference point being spaced apart from the desired target point, b) determining the coordinates of a corrected reference point taking account of a distorted gradient field of the examination device in such a way that, should the corrected reference point be used instead of the desired reference point, the examination device, on account of the distorted gradient field, acquires an imaging layer containing the desired reference point, c) correcting a possible local layer rotation between the desired imaging layer and the imaging layer actually acquired by the examination device on account of the distorted gradient field, by using the coordinates of the desired target point, the desired reference point, the corrected target point and the corrected reference point.

A possible local layer rotation as a consequence of a layer deformation of the imaging layer actually recorded by the examination device can be corrected in the examination device on the basis of the coordinates of the further reference point. In this way, it is also possible to correct deviations in the surroundings of the target point since a tilt of the imaging layer can be identified and compensated for by way of such a further reference point. Naturally, it is also possible to accordingly acquire even more further reference points and include these in the correction.

In this way, it is possible to compensate, e.g., nonlinearities in MRI recordings which occur on account of deviations of the gradient fields from the linear profile in the edge region.

According to an advantageous embodiment of the invention, provision is made for the coordinates of the target point determined by the measuring device to be transferred via a data interface to an evaluation apparatus of the examination apparatus. In this way, even an available imaging examination device can be upgraded with relatively little complexity so to be able to carry out the method according to the invention. In many cases, this can be realized by upgrading the software of the examination device. The examination device merely requires a data interface for feeding the coordinates determined by the measuring device. In respect of their coordinates, the further reference point or the further reference points can be transferred to the examination system in the same way as the coordinates of the target point, for example by way of the data interface.

According to an advantageous embodiment of the invention, provision is made for the desired imaging layer to be acquired by the examination device from a restricted examination region, with geometric distortions in the image representation increasing as a function of the distance from the center of the examination region.

According to an advantageous embodiment of the invention, provision is made for a method to be carried out in real time during an examination of an object to be examined.

In this context, "real time" means that the method can be carried out during a medical examination or medical intervention on a patient, and short time delays which may arise due to the data processing do not have a negative influence on the process.

The object specified at the outset is also achieved by a computer program having program code means, configured to carry out a method of the aforementioned type when the computer program is executed on a computer. The aforementioned advantages can also be realized thereby.

The object specified at the outset is also achieved by an examination device for examining an object layer-by-layer, the examination device being coupled to a measuring device and the examination device being configured to carry out a method of the aforementioned type in cooperation with the measuring device. The aforementioned advantages can also be realized thereby.

The invention will be explained in more detail below on the basis of an exemplary embodiment, using the drawings, in which.

Figure 1:
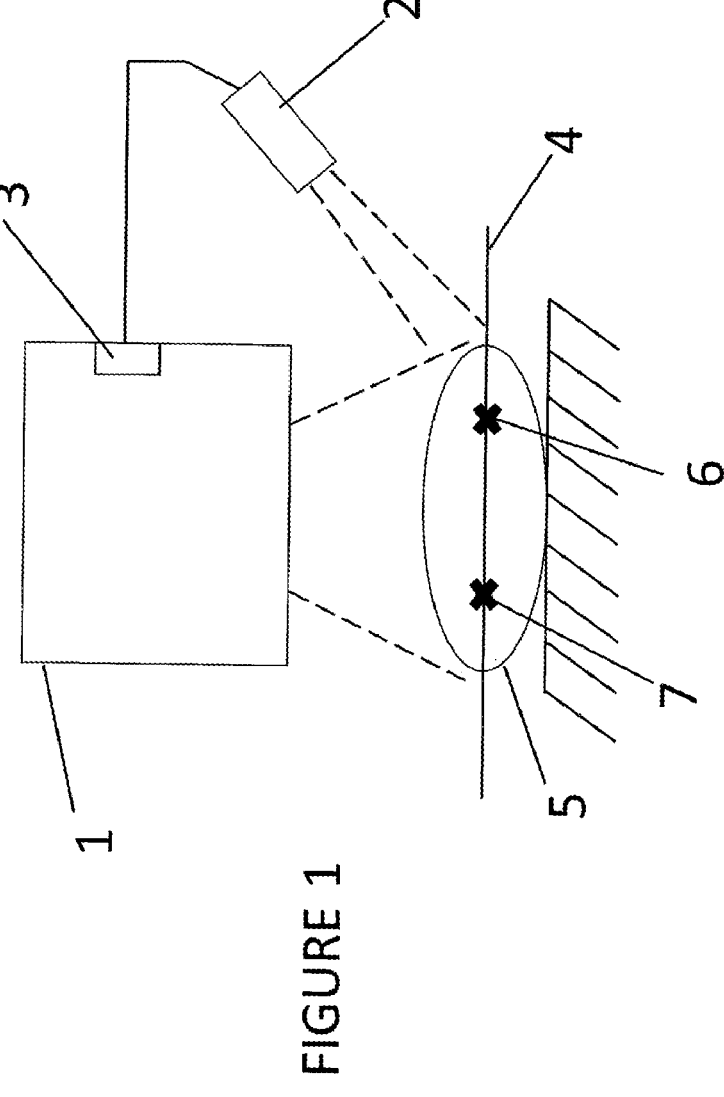
FIG. 1 shows an examination device and a measuring device.

FIG. 1 shows an examination device 1 and a measuring device 2. It is further possible to identify an object 5 to be examined, which is located in an examination region of the examination device 1 and in a measurement region of the measuring device 2. Moreover, a desired imaging layer 4 of the object 5 to be examined is marked in FIG. 1. A target point 6 and a further reference point 7 are marked in this desired imaging layer 4.

The coordinates of the target point 6 and optionally the coordinates of the further reference point 7 are determined after the desired imaging layer 4 was defined.

This can optionally be implemented by the measuring device 2. The measuring device 2 transmits the determined coordinates to the examination device 1 via a data interface 3. The examination device 1 is used to determine the coordinates of a corrected target point 6' taking account of a distorted gradient field of the examination device 1, in such a way that, should the corrected target point 6' be used instead of the desired target point 6, the examination device 1, on account of the distorted gradient field, acquires an imaging layer containing the desired target point 6.

The same can be carried out in respect of the coordinates of the further reference point 7, and so the corrected reference point 7' is additionally available. Only then is the imaging layer acquired by the examination device 1, to be precise on the basis of the coordinates of the target point 6, the further reference point 7, the corrected target point 6' and the corrected reference point 7' of the examination device 1. This ensures that the desired imaging layer 4 is actually acquired by the examination device 1 as imaging layer 4. Consequently, the image then visualized by the examination device 1 reliably shows the desired imaging layer 4 of the object 5 to be examined. Moreover, a possible local layer rotation between the desired imaging layer and the imaging layer actually captured by the examination device 1 on account of the distorted gradient field can be corrected.

Figure 2:
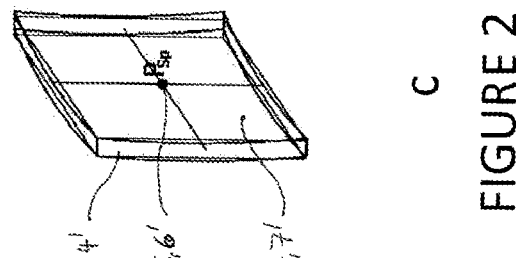
FIG. 2 shows a correction procedure on the layer position and layer rotation.
Figure 2:
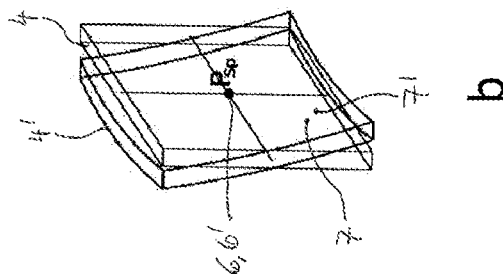
Figure 2:
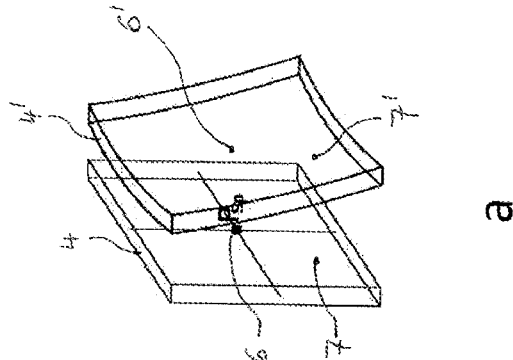

This correction procedure is now explained on the basis of the illustrations in FIG. 2. Image a) shows the desired imaging layer 4 and the imaging layer 4' actually recorded on account of the distortions and nonlinearities without the application of the correction method according to the invention. The actually recorded imaging layer 4' does not include the desired target point 6. Moreover, it has a different spatial orientation to the desired imaging layer 4.

The correction procedure using the target point 6 and the corrected target point 6' is depicted in image b). The examination device 1 now acquires an actual imaging layer 4' which contains the desired target point 6, that is to say there consequently is congruence between the desired target point 6 and the corrected target point 6' on account of the correction. However, it is evident that the spatial orientation of the actually acquired imaging layer 4' does not yet correspond to the desired imaging layer 4, that is to say a layer rotation is present.

If the correction is now augmented by the determination of the desired reference point 7 in the desired imaging layer 4 and the additionally determined corrected reference point 7', the layer rotation can also be corrected on account of the information about the angle difference between the layers 4, 4' now present. This is illustrated in image c). The correction of the layer rotation can be implemented particularly efficiently if a target point 6 and a reference point 7 arranged on a common straight line are defined, with the straight line being located in the desired imaging layer 4.

The peculiarity consists in the prospective correction of the layer selection before imaging, ensuring a recording of the desired layer even in the region where nonlinearities of the gradients have previously lost the target region from the layer. In general, the effect becomes more pronounced the further the plane of the layer is situated away from the center of the examination region of the examination device 1. Undistorted recordings arise as a result of additionally carrying out the standard correction within the plane of the layer. The method is likewise applicable to live imaging since the correction data can be calculated in advance and hence short computation times are possible.

The invention claimed is:

1. A method for operating an imaging examination device, wherein signals from an object to be examined are recorded and are determined and represented as sectional images and/or three-dimensional images of the object, comprising:

performing, prior in time to d) and d') and e), a) defining a desired imaging layer of the object to be examined, b) determining coordinates of a desired target point that is within the desired imaging layer, as determined coordinates of the desired target point, b') determining coordinates of a desired reference point that is within the desired imaging layer, as determined coordinates of the desired reference point, said desired reference point being spaced apart from the desired target point, c) determining coordinates of a corrected target point, as determined coordinates of the corrected target point, taking account of a distorted gradient field of the examination device in such a way that, should the determined coordinates of the corrected target point be used instead of the coordinates of the desired target point in a subsequent acquiring by the examination device of an imaging layer of the object, as a subsequent acquired imaging layer, the subsequent acquired imaging layer will contain, on account of a distorted gradient field of the examination device, the desired target point, c') determining coordinates of a corrected reference point, as determined coordinates of the corrected reference point, taking account of the distorted gradient field of the examination device in such a way that, should the determined coordinates of the corrected reference point be used instead of the determined coordinates of the desired reference point in the subsequent acquiring, by the examination device of the imaging layer of the object, the subsequent acquired imaging layer will contain, on account of the distorted gradient field of the examination device, the desired reference point, d) acquiring, by the examination device, of an actually acquired imaging layer of the object, wherein the acquiring by the examination device, of the actually acquired imaging layer of the object is configured using the step b) determined coordinates of the desired target point, the step b') determined coordinates of the desired reference point, the step c) determined coordinates of the corrected target point, and the step c') determined coordinates of the corrected reference point, such that the actually acquired imaging layer contains the target point, and contains the reference point, d') determining, as a determined layer rotation, a rotation between the step d') actually acquired imaging layer of the object and the step a) desired imaging layer, by a two-point rotation determination process that includes determining an angle between a first reference line that extends, in the desired imaging layer, through the step b) determined coordinates of the desired target point and the step c) determined coordinates of the desired reference point, and a second reference line that extends through the step b') determined coordinates corrected target point and the step c') determined coordinates of the corrected reference point, the determined layer rotation being said angle, e) reconstructing and visualizing an image by steps including correcting, based on the step d' determined layer rotation a spatial orientation of the step d) actually acquired imaging layer to correspond to a spatial orientation of the desired imaging layer.

2. The method as claimed in claim 1 wherein the acquiring of the actually acquired imaging layer by the examination device, is from a restricted examination region with geometric distortions in an image representation increasing as a function of a distance from a center of the restricted examination region.

3. The method as claimed in claim 1 wherein the method is carried out in real time during an examination of the object to be examined.

4. The method as claimed in claim 1 wherein the determining the coordinates of the desired target point and/or of the desired reference point comprises a measuring determination by a measuring device different from the examination device.

5. The method as claimed in claim 4, further comprising transferring the determined coordinates of the desired target point determined by the measuring determination by the measuring device via a data interface to an evaluation apparatus of the examination device.

6. A non-transient storage medium encoded with a computer program executable on a computer configured to carry out a method as claimed in claim 1.

7. A system comprising an examination device configured for examining an object layer-by-layer, the examination device being coupled to a measuring device configured to carry out a method as claimed in claim 1.

8. The method as claimed in claim 1, wherein the determining the coordinates of the desired target point and the coordinates of the desired reference point comprises a measuring determination by a measuring device different from the examination device.

9. The method as claimed in claim 8, further comprising transferring the coordinates of the desired target point and the coordinates of the desired reference point from the measuring device via a data interface to an evaluation apparatus of the examination device.

* * * * *